United States Patent [19]

Huang et al.

[11] Patent Number: 5,532,221
[45] Date of Patent: Jul. 2, 1996

[54] IONICALLY CROSSLINKED CARBOXYL-CONTAINING POLYSACCHARIDES FOR ADHESION PREVENTION

[75] Inventors: W. James Huang, Somerville; Douglas B. Johns, Milford; Richard L. Kronenthal, Fair Lawn, all of N.J.

[73] Assignee: Lifecore Biomedical, Inc., Chaska, Minn.

[21] Appl. No.: 192,336

[22] Filed: Feb. 4, 1994

Related U.S. Application Data

[63] Continuation-in-part of Ser. No. 680,955, Apr. 5, 1991, abandoned.

[51] Int. Cl.⁶ .................. A61K 31/715; C07H 13/02
[52] U.S. Cl. ................ 514/53; 514/54; 514/55; 514/56; 514/57; 514/59; 514/60; 514/62; 536/119; 536/121
[58] Field of Search .................. 514/53, 54, 55, 514/56, 57, 59, 60, 62; 536/119, 121

[56] References Cited

U.S. PATENT DOCUMENTS

| | | | |
|---|---|---|---|
| 4,024,073 | 5/1977 | Hirohiko et al. | 252/316 |
| 4,141,973 | 2/1979 | Balazs | 424/180 |
| 4,181,718 | 1/1980 | Norbert et al. | 424/180 |
| 4,442,258 | 4/1984 | Sunakawa et al. | 524/767 |
| 4,772,419 | 9/1988 | Malson et al. | 252/315.1 |
| 4,937,254 | 6/1990 | Sheffield et al. | 514/420 |
| 5,093,319 | 3/1992 | Higham et al. | 514/55 |

FOREIGN PATENT DOCUMENTS

| | | |
|---|---|---|
| 264719 | 12/1989 | Czechoslovakia ........... A61K 31/715 |
| 0138572A2 | 4/1985 | European Pat. Off. . |
| 0265561 | 10/1986 | European Pat. Off. . |
| WO86/00912 | 2/1986 | WIPO . |
| WO89/02445 | 3/1989 | WIPO . |
| WO90/10020 | 9/1990 | WIPO . |

OTHER PUBLICATIONS

Chem. Abstracts 114 (10):88722t A. Galatik, "Pharmaceutical preparation based on hyaluronic acid alkali metal salt complexes with multivalent metals", 1989.

Proc. Int. Conf. on Chitin & Chitosan, Conf. 4; Proc 1988 Aug. 24,1988, Y. Izumi, "The Influence of Metal Ions as Carboxymethyl–Chitin" pp. 519–522.

Chem Abst CA 100(6) ;36049v M. Mozisek Crosslinked, 1983. Carboxymethyl Cellulose with High Sorption Capacity.

Derwent AN 86–282502 abstract of JP-A-61 207 328, 1986 (Taisho Parmaceut. KK).

Derwent AN 79–32582B abstract of JP-A-54 036 388, 1979 (Submitomo Elec. Ind. KK).

J. Kost, "Chemically–modified polysaccharides for enzymatically–controlled oral drug delivery", Biomaterials vol. 11, Nov. 1990, pp. 695–698.

Schmut et al., Graefe's Arch Clin Exp Ophthalmol (1982) 218:311–314.

Primary Examiner—John Kight
Assistant Examiner—Everett White
Attorney, Agent, or Firm—Vidas, Arrett & Steinkraus

[57] ABSTRACT

A method of reducing post-operative adhesion formation by topically applying an ionically crosslinked carboxyl-containing polysaccharide or a pharmacologically acceptable salt thereof, e.g. sodium hyaluronate crosslinked with ferric chloride, to a site of surgical trauma.

15 Claims, No Drawings

IONICALLY CROSSLINKED CARBOXYL-CONTAINING POLYSACCHARIDES FOR ADHESION PREVENTION

BACKGROUND OF THE INVENTION

This is a continuation-in-part of Ser. No. 680,955 filed Apr. 5, 1991, now abandoned, which is hereby incorporated by reference herein.

This invention relates to a method of preventing post-operative adhesion formation. Adhesions are unwanted tissue growth occurring between layers of adjacent bodily tissue or between tissue and internal organs when the healing process begins following a surgical procedure. More specifically, the invention relates to such a method which employs the use of ionically crosslinked carboxyl-containing polysaccharides to control the incidence and extent of adhesion formation at a site of surgical trauma.

The medical and scientific community has extensively studied the therapeutic uses of carboxyl-containing polysaccharides and their water soluble salts for well over a decade. For example, U.S. Pat. No. 4,141,973 (the Balazs patent) discloses the use of a non-inflammatory hyaluronic acid (HA) fraction for numerous therapeutic applications. These applications include, among other things, the prevention of fibrous tissue formation, e.g., the prevention of adhesions; the protection of skin wounds; and the most successful application to date, the use of HA as a viscoelastic ophthalmic during ophthalmic surgery.

The prevention or reduction of adhesion formation following surgery requires a therapeutic agent which has an acceptable half life in bodily tissue. HA, in the free acid form or as its salt (sodium, potassium, etc.), is highly soluble in moist environments. This high solubility as well as susceptibility to naturally occurring enzymes leads to a very short half life of approximately 1 to 3 days in bodily tissue. While this may be acceptable for prevention of adhesions in some indications, for others a longer half life is desirable.

Accordingly, attempts have been made to increase the half life of HA and other carboxyl-containing polysaccharides without sacrificing the therapeutic efficiency of such compounds, particularly for adhesion prevention. For example, U.S. Pat. No. 4,772,419 discloses crosslinking HA with a polyfunctional crosslinking agent which creates ether, ester, or amide linkages. The covalently crosslinked HA forms a gel, and this gel is disclosed as being efficacious for the prevention of adhesions and accretion of tissues. PCT Application WO 89/02445 discloses a water-insoluble derivative of HA prepared by reacting HA with any of a number of different activating agents to prepare a covalently crosslinked HA fraction. PCT Application WO 86/00912 discloses crosslinking HA or other carboxyl-containing polysaccharides with a polyfunctional epoxide to prepare a degradable gel for the prevention of adhesions or accretions of bodily tissue.

Although the attempts to enhance the half life of HA as well as other carboxyl-containing polysaccharides by covalently crosslinking the chosen polysaccharide have met with some success, the biocompatibility and toxicity of the crosslinking agents used for the covalent bonding is unknown. Additionally, the degree of reduction in the incidence of adhesion prevention, although slightly better than HA in its uncrosslinked form, is still inadequate for numerous applications. Therefore, in view of the deficiencies of the prior art, it would be desirable to prepare a derivatized carboxyl-containing polysaccharide which is biocompatible with bodily tissue and exhibits a high degree of adhesion prevention or reduction relative to that of either the native or the covalently crosslinked carboxyl-containing polysaccharides described in the literature.

SUMMARY OF THE INVENTION

The invention is a method of reducing the incidence of post-operative adhesion formation. The invention comprises the step of topically applying as an adhesion preventative an effective amount of an ionically crosslinked carboxyl-containing polysaccharide or a pharmacologically acceptable salt thereof to a site of surgical trauma.

The adhesion preventative in preferred embodiments of this invention has a half life greater than that of the corresponding uncrosslinked polysaccharide, and comparable to that of a corresponding covalently crosslinked polysaccharide. When the adhesion preventative is topically applied to a site of surgical trauma, it exhibits an increased tendency to reduce the incidence of post-operative adhesion formation relative to that of either an uncrosslinked carboxyl-containing polysaccharide or a covalently crosslinked carboxyl-containing polysaccharide. Additionally, the crosslinking agents used for preparing the adhesion preventative are biocompatible and non-toxic to bodily tissue.

The method of this invention can be used in those applications requiring a reduction in the incidence of post-operative adhesion formation, or for any other application which could directly or indirectly benefit from such a therapeutic use, e.g. ophthalmic and orthopedic applications. The ionically crosslinked carboxyl-containing polysaccharide may also be useful as a drug delivery system, e.g. for delivery of wound healing agents, antibiotics, etc.

DETAILED DESCRIPTION OF THE INVENTION

For purposes of defining this invention, a carboxyl-containing polysaccharide is a polysaccharide containing at least one carboxyl group. The polysaccharide chosen may initially contain carboxyl groups or it may be derivatized to contain carboxyl groups. Examples of carboxyl-containing polysaccharides include, but are not limited to, carboxymethyl cellulose, carboxymethyl chitin, carboxymethyl chitosan, carboxymethyl starch, alginic acid, pectin, carboxymethyl dextran, and glucosaminoglycans such as heparin, heparin sulfate, chondroitin sulfate and HA. The most preferred carboxyl-containing polysaccharides are carboxymethyl cellulose, carboxymethyl chitin and HA. The most preferred carboxyl-containing polysaccharide is HA.

The adhesion preventative can employ a carboxyl-containing polysaccharide in the free acid form, or alternatively, a pharmacologically acceptable salt of the polysaccharide can be used. The preferred pharmacologically acceptable salts are alkali or alkaline earth metal salts. Preferably, the adhesion preventative employs the pharmacologically acceptable salt of the carboxyl-containing polysaccharide to prevent the formation of adhesions. Therefore, the most preferred adhesion preventative is sodium hyaluronate.

Carboxyl-containing polysaccharides which can be used to prepare the adhesion preventative are known compounds that are described, for example, in U.S. Pat. No. 4,517,295 and U.S. Pat. No. 4,141,973; and Handbook of Water Soluble Gums and Resins, Chapter 4, by Stelzer & Klug, published by McGraw-Hill, 1980. Processes for preparing the most preferred carboxyl-containing polysaccharide, HA, are illustrated in the Balazs patent, which details a procedure for extracting HA from rooster combs, and in U.S. Pat. No. 4,517,295 which describes a fermentation process for making HA. The HA used to make the adhesion preventative should be highly purified (medical grade quality) for surgical applications.

The crosslinking agents which can be used to ionically crosslink the carboxyl-containing polysaccharide are compounds which possess polyvalent cations, preferably trivalent cations, e.g. ferric chloride, aluminum chloride, chromium sulfate, and aluminum sulfate. The most preferred crosslinking agent is ferric chloride because of its low toxicity and biocompatibility with bodily tissue.

The crosslinking reaction typically occurs almost instantaneously when an aqueous polycation solution is contacted with an aqueous solution of at least 0.5 weight percent of the carboxyl-containing polysaccharide. The concentration of polycationic species present in the reaction mixture should be a concentration sufficient to crosslink at least 10 percent of the carboxyl groups of the polysaccharide. Preferably, the concentration of polycations will be sufficient to crosslink in the range of from about 60 to about 100 percent of the carboxyl groups of the polysaccharide and more preferably in the range of from 70 to 100 percent of the carboxyl groups of the polysaccharide and most preferably in the range of from 80 percent to 95 percent of the carboxyl group of the polysaccharide.

For example, sodium HA is a linear polysaccharide with a disaccharide repeat unit of sodium D-glucuronide and N-acetyl-D-glycocyamine which are linked by beta 1–3 linkages. A concentration of trivalent cation species sufficient to crosslink 60 percent of the carboxyl group would require a concentration of cations sufficient to provide 20 trivalent cations per 100 carboxyl groups. The concentration of trivalent cations per concentration of HA molecules would be dependent on the number of disaccharide repeating units present in each HA molecule. Preferably, the weight average molecular weight of the HA will be in the range of from about 550,000 to about 8,000,000 and most preferably in the range of from about 600,000 to about 2,000,000.

After the reaction, it is usually desirable to adjust pH to about neutral. In some instances, it is necessary to preadjust the polysaccharide solution pH to an acidic pH to prevent precipitation of the HA upon addition of the polycation solution. This often becomes necessary when strong ionic bonds are created, e.g. when the crosslinking agent used is ferric chloride.

An acceptable pH range for HA crosslinked with iron, chromium or aluminum cations is in the range form about pH 4.5 to about pH 8.0. The lower limit was based on sterile I.V. injection saline products which also have a low pH limit of 4.5, while the upper limit was selected to avoid basic pH. Results from preclinical studies indicate that pH within this range has no effect on efficacy. However, based on the pH dependence of gel strength, it is preferred that the pH is in the range of from about 4.5 to about 6. pH higher than 7 might adversely affect long term stability of the gel.

The crosslinking reaction utilizes a polysaccharide possessing anionic groups at each of the carboxyl sites. These anionic groups are ionically bound to the polyvalent cations. The ionically crosslinked polysaccharide, which represents the adhesion preventative used in the method of the invention, is characterized by its tendency to gradually disassociate into its separate ionic species when placed in an ionic medium, e.g. saline.

The viscosity of the adhesion preventative can be controlled by changing the concentration of polysaccharide in solution or by varying the concentration of polycation to control the crosslink density. The adhesion preventative may exist in the form of a gel at relatively high viscosities, or alternately, it may exist as a low viscosity fluid. Generally, the viscosity of crosslinked HA in an aqueous solutions should be at least 2,500 cps measured at room temperature with a Brookfield Model RTVDV-IICP viscometer (using spindle #40 shear rate=3.75 $\text{sec}^{-1}$ at 0.5 rpm for viscosities less than 6000 cps or a #52 spindle shear rate=1 $\text{sec}^{-1}$ at 0.5 rpm for viscosities greater than 6000 cps). Preferably the viscosity of the crosslinked HA will be in the range of from about 2,500 cps to about 250,000 cps and most preferably in the range of from about 2,500 cps to about 100,000 cps. The viscosity of the crosslinked HA, however, are process-dependent. Longer mixing time or higher shearing rate usually result in lower gel viscosity, although loss due to shear-thinning is reversible at crosslinking densities greater than 50 percent. Regardless of the viscosity which the adhesion preventative exhibits, it may exhibit an increased half life in comparison to an uncrosslinked polysaccharide because of its crosslinked structure.

As used herein, topical application refers to the administration of the adhesion preventative nonsystemically to the surface of the bodily tissue to be treated. The term "site of surgical trauma" is meant to include the site of tissue that has been injured in any way, and includes, for example, tissue sites that have undergone incision, drying, suturing, excision, abrasion, contusion, laceration, anastomosis, manipulation, prosthetic surgery, curettage, orthopedic surgery, neurosurgery, cardiovascular surgery, or plastic or reconstructive surgery. "Site of surgical trauma" also includes tissue that is adjacent to the injured tissue.

The method of this invention can be used to prevent post-operative adhesions in any animal that is susceptible to unwanted adhesion formation following surgery. Advantageously, the method is used to prevent adhesions from developing in mammals, preferably human beings.

The method of the invention is useful in any surgical procedure in which it is desired to inhibit the formation of post-surgical adhesions. It is thus broadly useful in all types of surgery in which adhesion formation can be a complication. For instance, the invention is useful in abdominal surgery, in gynecological surgery, in thoracic surgery, in orthopedic surgery affecting tendons, ligaments, etc., in neurological surgery affecting the dura mater, in liver surgery, and the like.

The adhesion preventative may be administered to the site of surgical trauma by any convenient mode such as, for example, by lavage, by coating directly on the site in a gel, cream, film, or foam, or by any other convenient mode. Preferably, the adhesion preventative is applied directly to the surgical site by injection through a syringe.

The administration of the adhesion preventative can occur at any time before significant wound healing has occurred. It is preferred and most convenient to administer the adhesion preventative during surgery or at the conclusion of the surgical procedure just prior to closing of the wound. However, in some cases, it may be desired to administer the adhesion preventative continually over a period of time.

An "effective amount" of adhesion preventative topically applied to the site of surgical trauma is an amount necessary to affect a reduction in the incidence of post-operative surgical adhesion formation. The amount applied will depend on numerous factors, most significantly of which is the surface area of the site of surgical trauma. Preferably, the amount of preventative applied should be enough to coat the entire area exposed to the surgical trauma, and if necessary or desired, an additional amount sufficient to coat bodily tissue adjacent to those areas actually exposed to the surgical trauma. The effective amount can be readily determined empirically.

The adhesion preventative used to prevent adhesion formation as described in this invention may also be used as a delivery vehicle for other adhesion prevention aids.

For example, the preventative can be used as a delivery vehicle for other well known adhesion preventatives, e.g. tolmetin or other non-steroidal anti-inflammatory drugs (NSAIDS) as described in U.S. Pat. No. 4,937,254, or tissue plasminogen activator (tPA) as described in European Patent No. 297860. Such a combination may create a synergistic effect between tolmetin and the adhesion preventative to significantly improve the efficacy of either therapeutic agent used alone. Alternatively, the adhesion preventative can be used not only for reducing adhesions but also as a delivery vehicle for other therapeutic agents, such as antibiotics, growth factors and other medicaments.

The following examples are intended to illustrate the claimed invention but are in no way intended to limit its scope.

EXAMPLE 1

Iron-Crosslinked HA Gel with High Crosslink Density as an Adhesion Preventative

(a) Preparation of Gel 0.634 grams of sodium hyaluronate with an average molecular weight of about 600,000 is dissolved in 39.36 g of water for injection in a glass beaker. After a homogeneous aqueous solution is obtained, 1.2 milliliters of a 1 N HCl is added with agitation to adjust solution pH. Then, 5.2 milliliters of a 1.5% ferric chloride solution is added with agitation. Finally, 2.493 ml of a 1.7N $NH_4OH$ solution is added with agitation until a homogeneous gel is obtained with a pH close to neutral. The resulting gel exhibits a viscosity of about 88,600 cps.

(b) Testing Protocol and Efficacy of Adhesion Preventative

Long Evans rats (each weighs about 250 g) are used in this study. Anaesthesia is accomplished with Ketamine (60 mg/Kg) and xylazine (10 mg/Kg) given intraperitoneally. To stimulate adhesions, the cecum is exteriorized and abrasions are made by wiping the cecum with gauze until punctate bleeding develops. Three 8 mm lesions are created on each side of the abdominal wall by removing a layer of the peritoneum and transverse abdominal muscle with a stainless steel biopsy punch. All accessible surfaces of the liver are abraded by rubbing them with the wooden end of a sterile swab. Six rats receive the ferric chloride crosslinked HA gel prepared by the process described in subpart (a) above. Three (3) ml of the ferric HA gel is applied to the cecum, biopsy punch sites and liver at closure of the incision.

Six rats in this study receive no treatment and serve as the control group. Six rats are treated with a lyophilized porous foam of HA covalently crosslinked with Crosslinker CX-100 Polyfunctional Aziridine Crosslinker (from ICI Resins, U.S.). A 6 cm diameter piece of the covalently crosslinked HA foam is cut up into smaller pieces and then placed over the abraded liver areas. Saline is applied to the foam until saturation to hydrate the foam.

Seven days after the surgery, the rats are sacrificed by carbon dioxide inhalation, and the sites are examined for the extent of adhesions. The number of sites and area of cecum adhesions are measured and recorded. The extent of liver adhesions at three sites is graded on a 0-to-6 scale, with a maximum total score of 18 representing the most severe adhesion formation. Ranking of the total scores of the three liver sites is used in statistical analysis of the experimental results. The results are summarized in Table 1.

TABLE 1

Efficacy of Iron Crosslinked HA Gel with High Crosslink Density for Reducing Adhesions

| Test Group | Rats with Cecal Adhesions | Avg No. of Adhesion Sites on Cecum | Rats with Liver Adhesions on all Lobes | Avg Total Liver Score (Rank) |
|---|---|---|---|---|
| Control | 5/6 | 1.67 | 6/6 | 11.33 (16.58) |
| Iron-Crosslinked HA Gel | 0/6 | 0 | 2/6 | 2.83 (4.25)*** |
| Covalently-Crosslinked HA Foam* | — | — | 2/4** | 6.50 (10.13) |

*HA foam applied to liver only.
**Two rats died.
***Statistically different from either control or HA foam.

The results indicate that the iron crosslinked HA gel shows significantly lower adhesions to the cecum and between liver lobes relative to the frequency of adhesions exhibited for an untreated control or a covalently crosslinked HA adhesion preventative.

EXAMPLE 2

Iron-Crosslinked HA Gel With Low Crosslink Density as an Adhesion Preventative The procedure described in Example 1 for preparing the iron crosslinked HA gel, as well as its testing protocol, are substantially repeated to prepare and evaluate an iron crosslinked HA gel with low crosslink density as an adhesion preventative. The following changes are made:

(a) Half of the amount of the ferric chloride solution is used to prepare the iron crosslinked HA gel to reduce the crosslink density, e.g. 2.6 ml of a 1.5% ferric chloride solution is added to the HA solution instead of 5.2 ml of solution which results in a gel of lower viscosity, i.e. 60,200 cps.;

(b) the adhesion preventative is compared with a lyophilized porous foam of HA which is covalently crosslinked with 1,4 butanediol digylcidyl ether instead of Polyfunctional Aziridine Crosslinker; and (c) the adhesion preventative is additionally compared with non-crosslinked sodium hyaluronate in saline solution exhibiting a viscosity of about 93,800 cps.

The results of the study are shown in Table 2.

TABLE 2

Efficacy of Iron Crosslinked HA Gel with Low Crosslink Density for Reducing Adhesions

| Test Group | Rats with Cecal Adhesions | Avg No. of Adhesion Sites on Cecum | Rats with Liver Adhesions on all Lobes | Avg. Total Liver Score (Rank)*** |
|---|---|---|---|---|
| Control | 6/6 | 2.00 | 6/6 | 9.50 (A) |
| Iron-Crosslinked HA Gel | 0/6 | 0 | 0/6 | 2.33 (C) |
| Covalently-Crosslinked Foam* | 1/5 | 0.2 | 3/5 | 7.00 (B) |
| Non-Crosslinked HA** | 2/5 | 0.6 | 3/5 | 5.40 (B) |

TABLE 2-continued

Efficacy of Iron Crosslinked HA Gel with Low Crosslink Density for Reducing Adhesions

| Test Group | Rats with Cecal Adhesions | Avg No. of Adhesion Sites on Cecum | Rats with Liver Adhesions on all Lobes | Avg. Total Liver Score (Rank)*** |
|---|---|---|---|---|

*Only five rats in this group.
**One rat died.
***Treatment groups with the same letter are not significantly different; the letter designation "C" represents the best statistical results for preventing adhesions.

The results indicate that the iron crosslinked HA gel shows significantly lower adhesions to the cecum and between liver lobes relative to the frequency of adhesions exhibited for an untreated control, a non-crosslinked HA adhesion preventative, or a covalently crosslinked HA adhesion preventative.

EXAMPLE 3

Aluminum-Crosslinked HA Gel as an Adhesion Preventative (a) Preparation of Gel 1.917 grams of sodium hyaluronate is dissolved in 118.1 grams of water for injection in a glass beaker. After a homogeneous aqueous solution is obtained, 7.2 milliliters of a 5% aluminum chloride hexahydrate solution is added with agitation. Then, 2.2 milliliters of a 1.7N $NH_4OH$ solution is added with agitation until a homogeneous gel is obtained with a pH close to neutral.

(b) Testing Protocol and Efficacy of Adhesion Preventative

Female New Zealand white rabbits of reproductive age (each weighed about 3.0 to 3.5 Kg) underwent uterine horn surgery to induce abdominal adhesion. The procedure involved making a midline incision into the abdomen, traumatizing both uterine horns, applying the crosslinked HA gel, and closing the wound. Twenty (20) rabbits are evenly divided into two groups: the control group, which receives no treatment before closing the wound, and aluminum-crosslinked HA treatment group. For the treated group, 10 milliliters of crosslinked HA gel (prepared according to subpart (a) above) is squirted directly on the uterus wherever adhesions are expected right before closing the wound. Seven days after surgery, each rabbit is sacrificed and a second procedure is performed to evaluate the extent of adhesions. Adhesions are subjectively scored on a scale from 0 (no adhesion) to 4 (severe adhesion) in increments of 0.5 in a blinded randomized manner. Table 3 summarizes the results.

TABLE 3

EFFICACY OF ALUMINUM CROSSLINKED HA GEL FOR REDUCING ADHESIONS

| TEST GROUP | NO. OF RABBITS TREATED | MEDIAN SCORE | MEAN RANK |
|---|---|---|---|
| CONTROL | 10 | 3.50 | 25.0 |
| ALUMINUM CROSSLINKED HA | 10 | 1.00 | 10.2 |

The results indicate that the use of an aluminum crosslinked HA gel as an adhesion preventative significantly reduces the incidence of post-operative adhesion formation.

EXAMPLE 4

Tissue Reaction and Half-Life of Iron-Crosslinked HA Gel

Ferric chloride crosslinked HA gel prepared from Example 2 (referred to as the "test" case) and sodium hyaluronate solution (referred to as the "control" case) are injected into the abdominal subcutaneous tissues of rats and analyzed at 1, 3, 7 and 14 days (4 rats/time period) to determine tissue reaction and absorption characteristics. Each animal has 2 test and 2 control 0.5 cc injection sites. Fixation is either by 10% formalin or a pH 7.4 fixative composed of 3% formaldehyde, 0.5% cetylpyridinium chloride and 30 mM NaCl in a 0.1 M phosphate buffer. The latter fixative forms an insoluble complex with glycosaminoglycans (ref: J. Histochem. and Cytochem., 33: 1060–1066, 1985). Hemantoxylin & eosin (H&E) staining is used with selected sites stained with Alcian blue in order to better visualize the HA. Tissue reaction grading is subjective.

Tissue reactions at test and control sites ranged from trace to slight at 1 and 3 days. Neutrophils and macrophages are present at day 1. By day 3 there are predominantly macrophages with smaller numbers of neutrophils and fibroblasts. Frequent macrophages at the day 3 test sites had a fine golden-brown intracytoplasmic pigment. HA is present at the majority of sites at 3 days.

At the day 7 test sites, coarse pigment-containing macrophages are the predominant cell type comprising a minimal to slight tissue reaction. The tissue reactions at the control sites are either zero or trace to minimal and composed predominantly of fibroblasts. There is apparent total absorption of HA at all control sites. A minimal amount of HA is still present at 3/7 test sites.

By 14 days the reactions at test sites are considered to be minimal with a decrease in the overall numbers of pigment-containing macrophages. The majority of control sites are difficult to localize due to a lack of residual tissue reaction. HA has been totally absorbed at all test and control sites by 14 days.

The tissue reactions of both samples are within acceptable limits.

EXAMPLE 5

Pre-clinical Efficacy Evaluation of Crosslinking

Formulae and procedure for preparing the gel at various crosslinking densities are summarized below with an example for making 100 g of a 1% HA (w/w) at 100% crosslinking density.

A. Sources of reagents

Sodium hyaluronate (HA): medical grade, LifeCore Biomedical Inc., molecular weight around 600,000.

Ferric chloride: $FeCl_3.6H_2O$, purified grade, Mallinckrodt, used as bulk pharmaceutical substance, prepared at a concentration of 1.5% (w/w) ferric chloride (not the hexahydrate) in 0.05N HCl before use.

Hydrochloric acid solution: N.F. grade, Mallinckrodt, 10% solution, diluted to 1N before use. Concentration of this solution is checked by pH measurement. A 1N HCL solution should have a pH value of 0.10. However, since most pH-meters tend to give fluctuating readings at this extremely low pH, strength of the solution is checked by measuring the pH of a 10:1 or a 100:1 dilution of the 1N solution, which yields most stable reading (pH=1.06 and 2.02 respectively).

Ammonium hydroxide solution: N.F. grade, Mallinckrodt, 27% $NH_4OH$ solution, diluted to 0.5N before use. Concentration is checked by pH measurement (pH=11.62).

B. Mixing

Step 1: Make an aqueous solution of HA by adding appropriate amount of water.

Example: 1.05 g of HA is mixed with 86.62 g of water under mild stirring (such as a magnetic stirring bar in a beaker for a small scale sample) until homogeneous solution is obtained. This step may take 2 to 24 hours, depending on the type and speed of mixer used, the concentration, and volume of the solution to be made.

Step 2: Add 3.14 ml of 1N HCl to acidify the HA solution. The solution can be easily mixed to homogeneity using the same stirring device in Step 1.

Step 3: Add 4.49 ml of 1.5% ferric chloride. Mixing is done with the same stirrer used in Steps 1 and 2, since viscosity of the acidified HA solution remains low after adding ferric chloride solution.

Step 4: Add 4.70 ml of 0.5N ammonia. Mixing is usually done by an overhead stirrer at a speed between 200 and 700 rpm. The significant increase in viscosity makes mixing much more difficult than in Steps 2 and 3. Mixing conditions might affect gel viscosity.

Step 5: Check pH of the product. Adjustments by adding more ammonia or hydrochloric acid are necessary if pH is not within the desired range. Viscosity should be checked after 8 to 16 hours since it may increase from the viscosity measured immediately after the mixing step, which shear-thins the product.

These formulae are empirical. Whenever possible, a small pilot batch should be made, pH and viscosity checked, before making a larger batch.

C. Apparatus and Methods

Viscosity was measured with a Brookfield Model RVTDV-IICP viscometer at 25° C., 0.5 rpm, unless otherwise specified. Viscosity less than 6,000 cps was measured with spindle #40 (shear rate=3.75 $sec^1$ at 0.5 rpm), unless otherwise specified. Samples with higher viscosity were measured with spindle #52 (shear rate=1 $sec^1$ at 0.5 rpm). For samples that exhibited thixotropic behavior, the initial viscosity (before the sample got shear-thinned in the viscometer) was taken as the viscosity of the sample.

Since HA crosslinked with iron (hereinafter, FeHA) viscosity is shear-rate-dependent, it is advisable to use the same spindle throughout, regardless of viscosity level, so that direct comparison between gels can be made. Since the Brookfield Model RVTDV-IICP viscometer yields the lowest shear rate when spindle #52 is used at 0.5 rpm, it is recommended that these two parameters (spindle #52, 0.5 rpm) be kept constant for all measurements in future work to enable consistent comparisons among samples.

pH was measured by either a Corning Model 240 or a Corning Model 250 pH-meter, calibrated with a pH-7 buffer and a pH-4 buffer (from Baxter Scientific Products).

Solutions/gels were prepared by using a Tekmar Type RCT-S19 magnetic stirrer with a stirring bar, or a Heidolph Model RZR-2000 overhead stirrer with various agitators, or a VirTishear homogenizer.

Rabbit Uterine Horn & Rabbit Sidewall Models

Two models, a rabbit uterine horn and a rabbit sidewall model, were utilized in a systematic study to evaluate the two key parameters that may affect the efficacy of FeHA formations, namely crosslinking density and gel viscosity.

Model Description

1) Uterine horn model: The abdomen was exposed through a ventral midline incision. The uterine horns were abraded on each side. Hemostasis was then achieved and a treatment group assigned. Adhesions were assessed by estimating the length of uterine horn with adhesions (maximum 5 cm) at 14±1 days after surgery.

2) Sidewall model: The abdomen was exposed through a ventral midline incision. The cecum was then located and exteriorized. An abrasion was made on the entire cecum by applying digital pressure with gauze (approximately 40 times), until punctate bleeding occurred. The large bowel was then located and abraded. The right sidewall was then exposed. A 3×5 cm lesion was created by scoring the sidewall with a scalpel blade and removing the peritoneum and transverse abdominous muscle. Area (percent) of the sidewall patch with adhesions was recorded at necropsy (7 days post-surgery) along with other parameters.

Tables 4, 5 and 6 summarize completed studies.

TABLE 4

SUMMARY OF STUDIES OF RABBIT SIDEWALL MODEL

| FORMULATION | VISCOSITY | pH | ADHESIONS[a] (NORMALIZED) |
|---|---|---|---|
| Control | n/a | n/a | 100% |
| 1.2% HA, 0% XL | 1,200 cps | 7.4 | 82% |
| 1.7% HA, 0% XL | 5,300 cps | 6.1 | 96% |
| 3.0% HA, 0% XL | 56,800 cps | 6.5 | 26% |
| 1.2% HA, 1% XL | 1,570 cps | 6.8 | 20% |
| 1.2% HA, 5% XL | 2,560 cps | 5.0 | 62% |
| 0.9% HA, 25% XL | 7,660 cps | 7.4 | 2% |
| 0.68% RA, 50% XL | 10,200 cps | 5.0 | 0% |
| 1.5% HA, 50% XL | 88,000 cps | 4.8 | 0% |
| 0.45% HA, 90% XL | 6,300 cps | 6.6 | 0% |
| 1.0% HA, 90% XL[b] | 51,400 cps | 4.9 | 0.1% |

[a] defined as % of sidewall adherent in treatment group divided by % of sidewall adherent in control group.
[b] average of two studies

TABLE 5

Summary of Studies of Rabbit Uterine Horn

| Treatment | N | Extent (cm) Average | SEM | Percent of Control |
|---|---|---|---|---|
| Control | 6 | 4.17 | 0.36 | 100% |
| 5% XL FeHA | 7 | 4.25 | 0.31 | 102% |
| 25% XL FeHA | 6 | 2.04** | 0.75 | 49% |

TABLE 5-continued

Summary of Studies of Rabbit Uterine Horn

| Treatment | N | Extent (cm) Average | SEM | Percent of Control |
|---|---|---|---|---|
| 50% XL FeHA | 7 | 1.11* | 0.43 | 27% |

*p 0.01,
**0.05 (Dunnett's t-test, compared with control)

TABLE 6

Summary of Studies of Rabbit Uterine Horn Model

| Formulation | Viscosity | pH | Adhesions[a] (Normalized) |
|---|---|---|---|
| Control | N/A | N/A | 100% |
| 1% HA, 0% XL | 1,200 cps | 7.4 | 104% (N = 7) |
| 2.75% HA, 0% XL | 30,200 cps | 5.7 | 97% (N = 3) |
| 3.65 HA, 0% XL | 99,600 cps | 6.6 | 80% (N = 6) |
| 1.2% HA, 5% XL | 1,970 cps | 5.5 | 102% (N = 7) |
| 1.0% HA, 25% XL | 10,200 cps | 7.7 | 91% (N = 7) |
| 1.0% HA, 50% XL | 39,200 cps | 5.7 | 77% (N = 7) |
| 0.9% HA, 25% XL | 7,660 cps | 7.2 | 49% (N = 6) |
| 0.68% HA, 50% XL | 8,840 cps | 7.9 | 27% (N = 7) |
| 0.45% HA, 90% XL | 3,140 cps | 5.0 | 65% (N = 6) |
| 0.68% HA, 90% XL | 14,900 cps | 4.9 | 54% (N = 6) |
| 1.0% HA, 90% XL | 44,900 cps | 7.3 | 48%[b] (N = 15) |
| 1.43% HA, 90% XL | 146,000 cps | 5.0 | 49% (N = 6) |

[a] average extent (cm) of treatment group divided by average extent (cm) of control group.
[b] average of two studies.

A clear trend towards improved efficacy with increasing crosslinking density was observed in the rabbit sidewall studies shown in Table 4. Ninety percent crosslinked FeHA virtually eliminated adhesions in the sidewall model. Lower viscosity formulation yield more variable results, though still efficacious in reducing adhesions formation. Among formulations with low viscosities, highly crosslinked FeHA with a lower HA concentration out performed FeHA with a similar viscosity having a lower crosslinking density.

The data in Tables 5 and 6 demonstrates that in the rabbit uterine horn model the efficacy of HA increases with crosslinking density. Table 5 demonstrates that increasing the crosslinking density from 5% to 50% significantly reduces the incidence of adhesions in the rabbit uterine horn model. Table 6 shows a clear trend toward improving efficacy with increasing the crosslinking density from 50% to 90% with similar concentration of HA. Additionally the reproducibility of adhesion prevention is significantly improved at higher crosslinking densities.

What is claimed is:

1. A method of reducing the incidence of post-operative adhesion formation in any animal that is susceptible to unwanted adhesion formation following surgery, comprising the step of topically applying as an adhesion preventative an effective amount of a carboxyl-containing polysaccharide, selected from the group consisting of hyaluronic acid and pharmacologically acceptable salts thereof having a weight average molecular weight of in the range of from about 550,000 to about 8,000,000 which has been ionically crosslinked with a trivalent cation provided in an amount sufficient to crosslink in the range of from about 60 to about 100 percent of the carboxyl groups of the carboxyl-containing polysaccharide, to a site of surgical trauma.

2. The method of claim 1 wherein the adhesion preventative is derived from hyaluronic acid, or an alkali or alkaline earth metal salt thereof.

3. The method of claim 2 wherein the adhesion preventative is derived from hyaluronic acid.

4. The method of claim 2 wherein the adhesion preventative is derived from sodium hyaluronate.

5. The method of claim 4 wherein the sodium hyaluronate is ionically crosslinked with a trivalent cation selected from the group consisting of iron, aluminum, and chromium provided in an amount sufficient to crosslink in the range of from about 60 to about 100 percent of the carboxyl groups of the sodium hyaluronate.

6. The method of claim 5 wherein the sodium hyaluronate is ionically crosslinked with iron.

7. The method of claim 2 wherein the adhesion preventative is administered in combination with another adhesion preventative aid.

8. The method of claim 7 wherein the adhesion prevention aid is a non-steroidal anti-inflammatory drug.

9. The method of claim 8 wherein the non-steroidal anti-inflammatory drug is tolmetin.

10. The method of claim 2 wherein the adhesion preventative is administered in combination with an agent selected from the group consisting of an antibiotic and a growth factor.

11. The method of claim 1 wherein the adhesion preventative is applied directly to the site of surgical trauma in one application.

12. The method of claim 11 wherein the adhesion preventative is applied during surgery or at the conclusion of surgery prior to closing.

13. The method of claim 1 wherein the adhesion preventative is made from hyaluronic acid crosslinked with a trivalent cation selected from the group consisting of iron, aluminum and chromium.

14. The method of claim 13 wherein the viscosity of the adhesion preventative is in the range of from about 2,500 cps to about 250,000 cps.

15. An adhesion preventative comprising a sterile non-inflammatory hyaluronic acid fraction having a weight average molecular weight of in the range of from about 550,000 to about 8,000,000 having carboxyl acid groups which are ionically crosslinked by at least one trivalent cation selected from the group consisting of iron, aluminum and chromium wherein from about 60 to about 100 percent of the carboxyl acid groups have been ionically crosslinked by said trivalent cations and the adhesion preventative has a viscosity of at least 2,500 cps.

* * * * *